(12) United States Patent
Wadhwa et al.

(10) Patent No.: US 11,230,516 B2
(45) Date of Patent: Jan. 25, 2022

(54) METHODS AND SYSTEMS FOR PURIFYING 1,3-BUTADIENE FROM A C4 HYDROCARBON STREAM

(71) Applicant: SABIC Global Technologies B.V., Bergen op Zoom (NL)

(72) Inventors: Kuldeep Wadhwa, Geleen (NL); Antonio Matarredona, Geleen (NL); Radu Ignat, Geleen (NL); Sekhar Mamilla, Geleen (NL); Christoph Roosen, Geleen (NL); Alex Londono, Geleen (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/375,208

(22) Filed: Apr. 4, 2019

(65) Prior Publication Data

US 2019/0233351 A1 Aug. 1, 2019

Related U.S. Application Data

(62) Division of application No. 15/763,743, filed as application No. PCT/IB2016/056573 on Nov. 1, 2016, now Pat. No. 10,384,991.

(Continued)

(51) Int. Cl.
*C07C 7/148* (2006.01)
*C07C 7/05* (2006.01)
*C07C 11/167* (2006.01)

(52) U.S. Cl.
CPC ............ *C07C 7/14875* (2013.01); *C07C 7/05* (2013.01); *C07C 11/167* (2013.01)

(58) Field of Classification Search
CPC .......... C07C 7/14875; C07C 7/148883; C07C 11/167; B01J 8/00; B01J 10/00; B01J 14/00

(Continued)

(56) References Cited

U.S. PATENT DOCUMENTS

| 2,847,487 A | 8/1958 | Kestner et al. | 260/681.5 |
| 2,963,523 A | 12/1960 | Hochgraf | 260/681.5 |

(Continued)

FOREIGN PATENT DOCUMENTS

| CH | 247438 A | 1/1948 |
| RU | 2276129 C2 | 5/2006 |

(Continued)

OTHER PUBLICATIONS

Adzima et al., "Vinyl-Triazolium Monomers: Versatile and New Class of Radically Polymerizable Ionic Monomers," *Journal of Polymer Science Part A: Polymer Chemistry*, 52.3:417-423 (2014).

(Continued)

*Primary Examiner* — Thuan D Dang
(74) *Attorney, Agent, or Firm* — Norton Rose Fulbright US LLP

(57) ABSTRACT

The presently disclosed subject matter relates to methods and systems for purifying 1,3-butadiene from a $C_4$ hydrocarbon stream. An example method includes introducing a $C_4$ hydrocarbon stream including 1,3-butadiene and acetylenes to an organic azide in the presence of a catalyst to generate a first stream including triazole, separating triazole from the first stream to produce a second stream including 1,3-butadiene, and distilling 1,3-butadiene from the second stream to produce a purified 1,3-butadiene product stream.

14 Claims, 3 Drawing Sheets

100

Introducing a $C_4$ hydrocarbon stream including 1,3-butadiene and acetylenes to an organic azide in the presence of a catalyst to generate a first stream — 101

Separating the triazole from the first stream to produce a second stream including 1,3-butadiene — 102

Distilling 1,3-butadiene from the second stream to produce a purified 1,3-butadiene product stream — 103

Related U.S. Application Data

(60) Provisional application No. 62/253,914, filed on Nov. 11, 2015.

(58) Field of Classification Search
USPC .................. 422/608, 610; 585/810, 862, 863
See application file for complete search history.

(56) References Cited

U.S. PATENT DOCUMENTS

| | | | |
|---|---|---|---|
| 3,837,144 A | 9/1974 | Lewis | 55/64 |
| 3,898,298 A | 8/1975 | Desiderio et al. | 260/681.5 |
| 7,375,234 B2 | 5/2008 | Sharpless et al. | 548/255 |
| 2014/0163263 A1* | 6/2014 | Wollrab | C07C 29/149 |
| | | | 568/885 |

FOREIGN PATENT DOCUMENTS

| | | |
|---|---|---|
| WO | WO2001085656 A1 | 11/2001 |
| WO | WO2008048733 A1 | 4/2008 |

OTHER PUBLICATIONS

Hu et al., "Microporous metal-organic framework with dual functionalities for highly efficient removal of acetylene from ethylene/acetylene mixtures," *Nature Communications*, 6:7328 (2015), 9 pages.

Ng et al., "Comparing the Reactivity of Alkynes and Alkenes on Silicon (100) Surfaces," *Langmuir*, 25(24):13934-13941 (2009).

Written Opinion and International Search Report from PCT/IB2016/056573, dated Feb. 8, 2017, 10 pages.

Qiu et al. "Advances in Click Chemistry." Progress in Chemistry. vol. 23, No. 4. Apr. 2011. 12 Pages. English Abstract Provided.

*Chemical Encyclopedia*. vol. 1. Editor-in-Chief I. L. Knunyants. Soviet Encyclopedia Publishing House. Moscow. 1988. p. 49, Column 73, Section 3-9, Section "Azid." English Translation Provided.

* cited by examiner

METHODS AND SYSTEMS FOR PURIFYING 1,3-BUTADIENE FROM A C4 HYDROCARBON STREAM

CROSS-REFERENCE TO RELATED APPLICATIONS

This application is a divisional of U.S. application Ser. No. 15/763,743, which is a national phase application under 35 U.S.C. § 371 of International Application No. PCT/IB2016/056573 filed Nov. 1, 2016, which claims priority to U.S. Provisional Patent Application No. 62/253,914 filed Nov. 11, 2015. The entire contents of each of the above-referenced disclosures is specifically incorporated by reference herein without disclaimer.

FIELD

The presently disclosed subject matter relates to methods and systems for purifying 1,3-butadiene from a $C_4$ hydrocarbon stream.

BACKGROUND 1,3-butadiene can be a valuable petrochemical product. It is a simple conjugated diene and can be a useful monomer in the production of synthetic rubber, adiponitrile, and chloroprene, among other materials. It also can be used in the Diels-Alder reaction to produce cycloalkanes and cycloalkenes.

1,3-butadiene is a component in $C_4$ hydrocarbon streams produced by cracking processes, e.g., steam cracking of naphtha, gas cracking, and catalytic cracking of gas oil and/or vacuum gas oil. $C_4$ hydrocarbon fractions are separated from lighter and heavier hydrocarbons using a fractional distillation column, such as a debutanizer. $C_4$ hydrocarbon streams can include butane, isobutane, isobutene, 1-butene, trans-2-butene, cis-2-butene, 1,3-butadiene, 1,2-butadiene, methylacetylene, ethylacetylene, vinylacetylene, and/or other components. It can be desirable to further isolate 1,3-butadiene from other components to produce a purified 1,3-butadiene stream.

Because 1,3-butadiene has low relative volatility compared to other components in a $C_4$ hydrocarbon stream, it is often separated using extractive distillation. Thus, purification of 1,3-butadiene from $C_4$ hydrocarbons can be carried out in two stages of extractive distillation: (1) to separate butanes and butenes to produce crude butadiene; and (2) to separate vinyl- and ethyl-acetylenes from crude butadiene. Extractive distillation may be followed by conventional distillation to remove methylacetylene. Because of the large amounts of solvent involved in extractive distillation, this process can be highly energy intensive. Further, separated acetylenes are often sent to a flare, and because of risk of explosion, must be diluted with valuable 1,3-butadiene.

Certain methods of purifying 1,3-butadiene are known in the art. U.S. Pat. No. 2,847,487 discloses a pre-wash containing cuprous ammonium acetate solution to form copper acetylides from acetylenes in crude butadiene. U.S. Pat. No. 2,963,523 discloses a pre-wash system including the recovery of butadiene from the pre-wash solvent by desorption. U.S. Pat. No. 3,898,298 discloses a method of selectively hydrogenating vinylacetylenes in a crude butadiene stream by reaction with hydrogen in the presence of a palladium and aluminum catalyst.

There is an interest in alternative methods of purifying 1,3-butadiene. One technique uses "click chemistry," a term sometimes applied to reactions that have high yield and produce products that are easily separated. An azide-alkyne cycloaddition reaction is a simple reaction that can be employed to remove acetylenes from 1,3-butadiene. In the azide-alkyne cycloaddition reaction, an organic azide reacts with acetylenes to form a triazole. For example, U.S. Pat. No. 7,275,234 discloses a method of forming cycloaddition triazoles from organic azides and terminal acetylenes in the presence of a catalyst.

There remains a need for improved methods of purifying 1,3-butadiene from a $C_4$ hydrocarbon stream.

SUMMARY OF THE DISCLOSED SUBJECT MATTER

The presently disclosed subject matter relates to methods and systems for purifying 1,3-butadiene from a $C_4$ hydrocarbon stream.

The presently disclosed subject matter provides methods for isolating 1,3-butadiene from a $C_4$ hydrocarbon stream including introducing the $C_4$ hydrocarbon stream to an organic azide in the presence of a catalyst to generate a first stream including 1,3-butadiene and a triazole and separating the triazole from the first stream to produce a second stream including 1,3-butadiene.

In certain embodiments, the $C_4$ hydrocarbon stream can include 1,3-butadiene, one or more butanes, one or more butenes, and one or more acetylenes. The one or more acetylenes can be ethylacetylene or vinylacetylene. The organic azide can include a hydrocarbon moiety and an azide group. In certain embodiments, the organic azide includes one or more of an alkyl azide, vinyl azide, allyl azide, aryl azide, and/or benzyl azide. The catalyst can include a metal ion, which can be one of Cu, Au, Ag, Hg, Cd, Zr, Ru, Fe, Co, Pt, Pd, Ni, Rh, Ti and W.

In certain embodiments, the second stream includes 1,3-butadiene, one or more butanes, and one or more butenes. The method can further include distilling the second stream in the presence of a first solvent to produce a raffinate stream and a third stream including 1,3-butadiene. The raffinate stream can include one or more butanes and one or more butenes.

In certain embodiments, the method can further include stripping the third stream to produce a regenerated solvent stream and a fourth stream including 1,3-butadiene. The method can further include recycling the regenerated solvent stream to a distillation unit. The method can further include distilling the fourth stream to produce a purified product stream including 1,3-butadiene. Distilling the fourth stream can use a second solvent. The first and/or second solvent can contain one or more of water, acetonitrile, N-methylpyrrolidone, furfural, dimethylformamide, acetone, and dimethylacetamide. The first and second solvents can be the same material.

The presently disclosed subject matter further provides a method for purifying 1,3-butadiene from a $C_4$ hydrocarbon stream including 1,3-butadiene and one or more acetylenes, including introducing the $C_4$ hydrocarbon stream to an organic azide in the presence of a catalyst to generate a first stream including 1,3-butadiene and a triazole, separating the triazole from the first stream to produce a second stream including 1,3-butadiene, one or more butanes, and one or more butenes, and distilling the second stream in the presence of a first solvent to produce a raffinate stream including one or more butanes and one or more butenes and a third stream including 1,3-butadiene.

The disclosed subject further provides another method for purifying 1,3-butadiene from a $C_4$ hydrocarbon stream including 1,3-butadiene and one or more acetylenes, including distilling the $C_4$ hydrocarbon stream in the presence of a first solvent to produce a raffinate stream including one or more butanes and one or more butenes and a first stream including 1,3-butadiene and one or more acetylenes, introducing the first stream to an organic azide in the presence of a catalyst to generate a second stream including 1,3-butadiene and a triazole, and separating the triazole from the second stream to produce a third stream including 1,3-butadiene.

The disclosed subject matter further provides systems for purifying 1,3-butadiene from a $C_4$ hydrocarbon stream. In certain embodiments, an exemplary system can include an azide-alkyne cycloaddition reactor and a first distillation unit coupled to the azide-alkyne cycloaddition reactor. The system can further include a second distillation unit coupled to the first distillation unit. In certain embodiments, the first distillation unit can be downstream from the azide-alkyne cycloaddition reactor. In other certain embodiments, the azide-alkyne cycloaddition reactor can be downstream from the first distillation unit.

DETAILED DESCRIPTION

The presently disclosed subject matter relates to methods and systems for purifying 1,3-butadiene from a $C_4$ hydrocarbon stream including 1,3-butadiene and one or more acetylenes.

Figure 1:
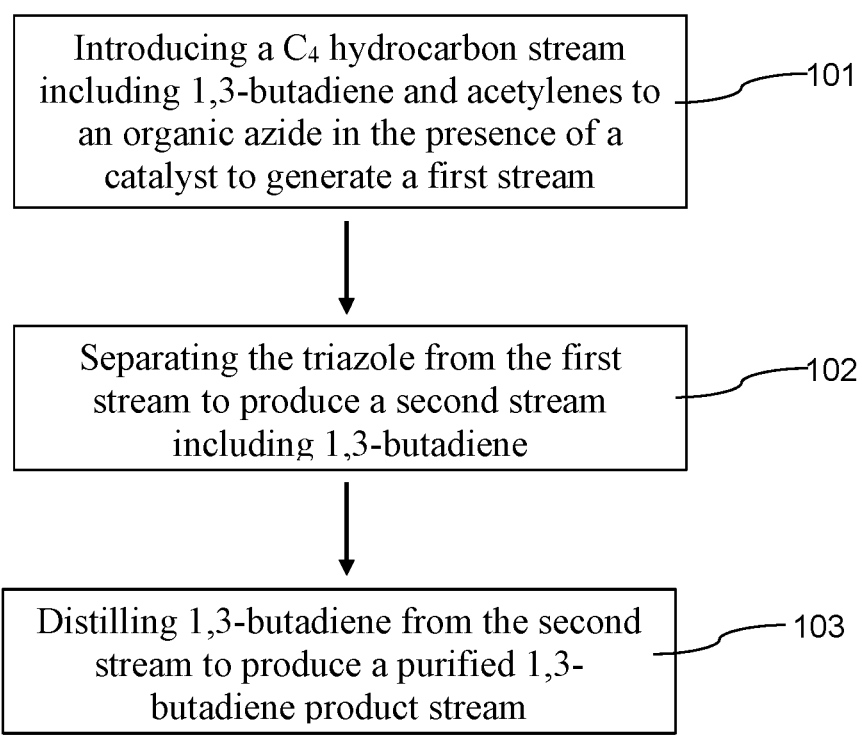
FIG. 1 depicts a method for purifying 1,3-butadiene from a $C_4$ hydrocarbon stream according to one exemplary embodiment of the disclosed subject matter.

The presently disclosed subject matter provides a method for the purification of 1,3-butadiene from a $C_4$ hydrocarbon stream by reacting acetylenes in a $C_4$ hydrocarbon stream with an organic azide to generate a stream containing 1,3-butadiene and a triazole. For the purpose of illustration and not limitation, FIG. 1 is a schematic representation of an exemplary method according to a non-limiting embodiment of the disclosed subject matter.

In certain embodiments, the method 100 can include introducing a $C_4$ hydrocarbon stream including 1,3-butadiene and one or more acetylenes to an organic azide to generate a crude product stream 101. The $C_4$ hydrocarbon stream of the presently disclosed subject matter can originate from various sources. For example, and not by way of limitation, a $C_4$ hydrocarbon stream can be generated by steam cracking of naphtha, mixed gas (e.g., ethane and liquid petroleum gas (LPG)) cracking and fluid catalytic cracking (FCC) of gas oil and/or vacuum gas oil. The $C_4$ hydrocarbon stream can include olefins, paraffins and/or 1,3-butadiene. For example, and not by way of limitation, the $C_4$ hydrocarbon stream can include 1,3-butadiene, 1,2-butadiene, isobutene, normal butane (n-butane), 1-butene, trans-2-butene, cis-2-butene, vinylacetylene, ethylacetylene, methylacetylene or combinations thereof.

As used herein, the term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

The organic azide for use in the presently disclosed method can be any hydrocarbon moiety containing an azide group. For example, and not by way of limitation, the organic azide can be an alkyl azide, vinyl azide, allyl azide, aryl azide, benzyl azide or any combination thereof.

In certain embodiments, the organic azide reacts with acetylenes in the $C_4$ hydrocarbon stream through an azide-alkyne cycloaddition reaction and forms a crude product stream including triazoles. Azide-alkyne cycloaddition can alternatively be termed "Huigen cycloaddition." In certain embodiments, the method includes performing the azide-alkyne cycloaddition reaction at a temperature from about 20° C. to about 150° C. In certain embodiments, the reaction can be performed at a pressure from about atmospheric to about 10 bar.

In certain embodiments, the method can further include conducting the azide-alkyne cycloaddition reaction in the presence of a catalyst. Catalysts for use in the presently disclosed subject matter can be any catalyst suitable for azide-alkyne cycloaddition. By way of example, and not limitation, the catalyst can include a metal salt having a metal ion, such as Cu, Au, Ag, Hg, Cd, Zr, Ru, Fe, Co, Pt, Pd, Ni, Rh, Ti, and W. In certain embodiments, the metal ion is Cu(I), Cu(II), Ag, or Ru. The catalyst can further include a ligand. By way of example, and not limitation, the ligand can include a cyanide, nitrile, isonitrile, acetonitrile, amine, nitrogen bearing heterocycle, carboxylate, halide, alcohol, thiol, sulfide, phosphine, phosphite, or water.

In certain embodiments, the method 100 can further include separating triazoles from the crude product stream to create a second stream 102. Triazoles may be removed by any method known in the art for the separation of triazoles from a $C_4$ hydrocarbon stream.

The selective reaction of acetylenes to form triazoles and the removal of triazoles from the crude product stream will result in a second stream containing less than about 1% w/w acetylenes, less than about 0.1% w/w acetylenes, less than about 0.01% w/w acetylenes, or no acetylenes.

In certain embodiments, the method 100 can include distilling 1,3-butadiene from the second stream to produce a third stream including 1,3-butadiene, and a raffinate stream including butanes and/or butenes. In certain embodiments, the method includes providing a solvent to a distillation column for extractive distillation. The extractive distillation solvent may be any solvent known in the art to be suitable for the distillation of 1,3-butadiene from $C_4$ hydrocarbons. In particular embodiments, the solvent can be a solvent in which butanes and butenes, e.g., within the second stream, are less soluble as compared to 1,3-butadiene. Example solvents include, but are not limited to, polar solvents, such as water, acetonitrile, N-methylpyrrolidone, furfural, dimethylformamide, acetone, dimethylacetamide or combinations thereof.

In certain embodiments, the method can include removing the raffinate stream from the distillation column. In certain embodiments, the raffinate stream includes the hydrocarbons present within the $C_4$ hydrocarbon feed that are less soluble in the solvent. In certain embodiments, the raffinate stream can include butanes and/or butenes, for example, and not by way of limitation, isobutene, normal butane (n-butane), 1-butene, trans-2-butene, and/or cis-2-butene.

In certain embodiments, the distillation of 1,3-butadiene from the second stream to produce a third stream including 1,3-butadiene can be performed at a temperature from about 10° C. to about 150° C., or from about 15° C. to about 100° C., from about 20° C. to about 70° C. In certain embodiments, the distillation can be performed at a pressure from about 1 bar to about 20 bar, from about 2 bar to about 10 bar, or from about 3 bar to about 8 bar.

It should be noted that the step of distilling 1,3-butadiene from the second stream, i.e., the $C_4$ hydrocarbon stream, to produce a third stream and a raffinate stream can be performed before or after the azide-alkyne cycloaddition reaction. In particular embodiments, the azide-alkyne cycloaddition reaction is conducted prior to distilling 1,3-butadiene from the $C_4$ hydrocarbon stream in order to increase throughput and decrease the relative amount of solvent needed for extractive distillation.

In certain embodiments, the third stream including 1,3-butadiene is purified further to create a purified 1,3-butadiene stream. In particular embodiments, the third stream is purified by distillation, by way of example, and not limitation, continuous or batch fractional distillation, vacuum distillation, azeotropic distillation, extractive distillation, reactive distillation and/or steam distillation.

The methods of the presently disclosed subject matter can provide improved recovery of 1,3-butadiene from $C_4$ hydrocarbon streams. In certain embodiments, greater than about 90%, greater than about 95%, or greater than about 99% of 1,3-butadiene is recovered from a $C_4$ hydrocarbon stream.

Figure 2:
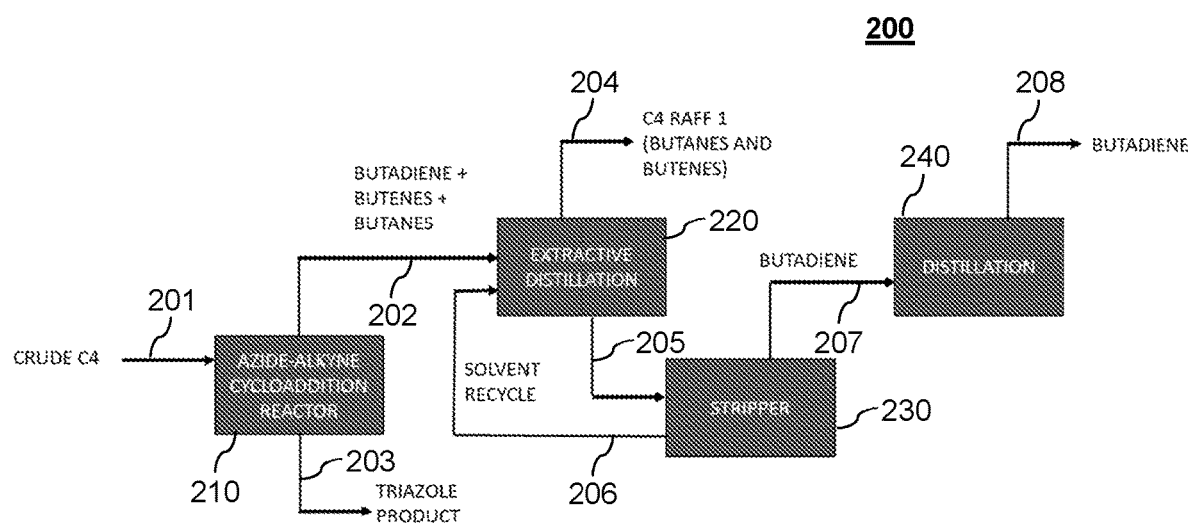
FIG. 2 depicts a system for purifying 1,3-butadiene from a $C_4$ hydrocarbon stream according to one exemplary embodiment of the disclosed subject matter.

The presently disclosed subject matter further provides systems for purifying 1,3-butadiene from a $C_4$ hydrocarbon stream including 1,3-butadiene and one or more acetylenes. For the purpose of illustration, and not limitation, FIG. 2 is a schematic representation of an exemplary system according to a non-limiting embodiment of the disclosed subject matter.

The system 200 can include an azide-alkyne cycloaddition reactor 210. The reactor can be any reactor type suitable for an azide-alkyne cycloaddition reaction. By way of example, but not limitation, such reactors include fixed bed reactors, such as tubular fixed bed reactors and multi-tubular fixed bed reactors, fluidized bed reactors, such as entrained fluidized bed reactors and fixed fluidized bed reactors, and slurry bed reactors such as three-phase slurry bubble columns and ebullated bed reactors.

The system 200 can further include one or more feed lines 201 coupled to the azide-alkyne cycloaddition reactor 210. The one or more feed lines 201 can be used to transfer a $C_4$ hydrocarbon stream including 1,3-butadiene and acetylenes to the reactor. In certain embodiments, the one or more feed lines transfer an organic azide to the reactor.

"Coupled" as used herein refers to the connection of a system component to another system component by any means known in the art. The type of coupling used to connect two or more system components can depend on the scale and operability of the system. For example, and not by way of limitation, coupling of two or more components of a system can include one or more joints, valves, transfer lines or sealing elements. Non-limiting examples of joints include threaded joints, soldered joints, welded joints, compression joints and mechanical joints. Non-limiting examples of fittings include coupling fittings, reducing coupling fittings, union fittings, tee fittings, cross fittings and flange fittings. Non-limiting examples of valves include gate valves, globe valves, ball valves, butterfly valves and check valves.

In certain embodiments, the system 200 further includes a triazole transfer line 203 coupled to the reactor 210 for removing triazole products. In certain embodiments, a first butadiene transfer line 202 is coupled to the reactor 210 for transferring a stream containing 1,3-butadiene and other $C_4$ hydrocarbons to a first distillation unit 220 for extractive distillation.

The first distillation unit for use in the presently disclosed subject matter can be any type suitable for extractive distillation known in the art. It can be adapted to continuous or batch distillation. It can be coupled to one or more condensers and one or more reboilers. It can be a stage or packed column, and can include plates, trays and/or packing material. It can be coupled to one or more transfer lines.

In certain embodiments, the first distillation unit 220 is coupled to one or more transfer lines 204, 205. In particular embodiments, a raffinate transfer line 204 removes raffinate including butanes and butenes from the first distillation unit 220. In particular embodiments, a solvent transfer line 205 removes the spent solvent containing 1,3-butadiene from the first distillation unit 220. In particular embodiments, the solvent transfer line 205 is also coupled to a stripper 230 for regenerating the solvent. In particular embodiments, a solvent recycle line 206 is coupled to the stripper 230 and the first distillation unit 220 for transferring regenerated solvent to the first distillation unit.

In certain embodiments, a second butadiene transfer line 207 is coupled to the stripper 230 for removing a stream containing 1,3-butadiene from the stripper. In particular embodiments, the second butadiene transfer line is coupled to a second distillation unit 240 for further purification of 1,3-butadiene. In particular embodiments, the second distillation unit 240 is coupled to a product line 208 for removing purified 1,3-butadiene from the system.

Figure 3:
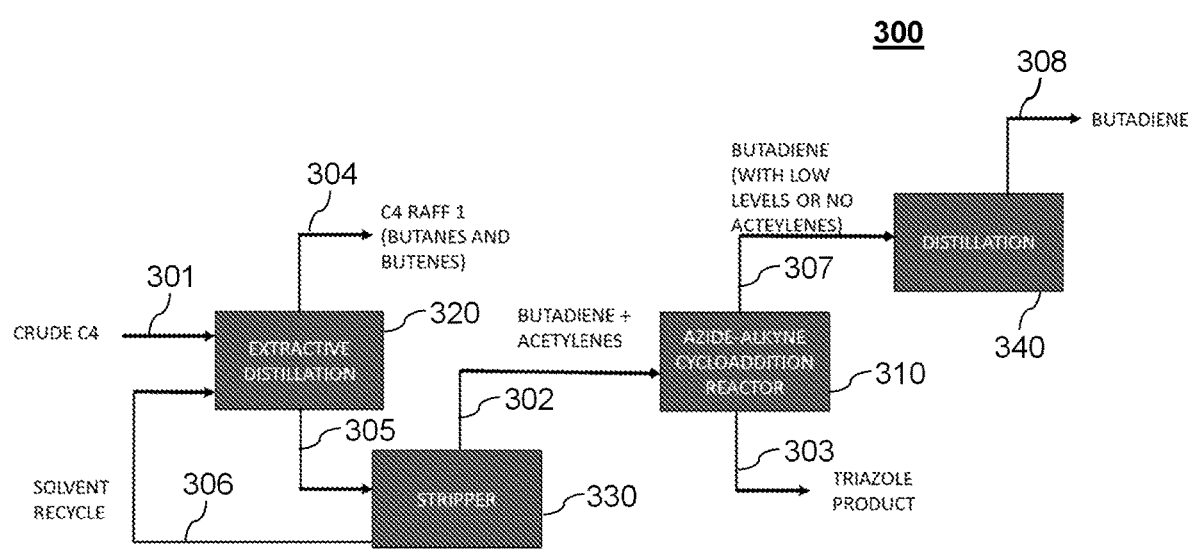
FIG. 3 depicts a system for purifying 1,3-butadiene from a $C_4$ hydrocarbon stream according to one alternative exemplary embodiment of the disclosed subject matter.

For the purpose of illustration and not limitation, FIG. 3 is a schematic representation of an alternative exemplary system according to a non-limiting embodiment of the disclosed subject matter. In an alternative embodiment, the azide-alkyne cycloaddition reactor 310 is downstream from the first distillation unit 320. In this embodiment, a raffinate transfer line 304 is coupled to the first distillation unit 320 for removing butanes and butenes from the $C_4$ hydrocarbon stream prior to the azide-alkyne cycloaddition reactor 310.

In particular embodiments according to this alternative system 300, a stripper 330 is coupled to the first distillation unit 320. In particular embodiments, a butadiene transfer line 302 is coupled to the stripper 330 for transferring a stream containing 1,3-butadiene and acetylenes to the azide-alkyne cycloaddition reactor 310. In particular embodiments, the system 300 can further include a second distillation unit 340 for further purification of 1,3-butadiene.

The presently disclosed systems can further include additional components and accessories including, but not limited to, one or more gas exhaust lines, cyclones, product discharge lines, reaction zones, heating elements and one or more measurement accessories. The one or more measurement accessories can be any suitable measurement accessory known to one of ordinary skill in the art including, but not limited to, pH meters, flow monitors, pressure indicators, pressure transmitters, thermowells, temperature-indicating controllers, gas detectors, analyzers and viscometers. The components and accessories can be placed at various locations within the system.

The methods and systems of the presently disclosed subject matter can have advantages over certain existing technologies, including improved recovery of 1,3-butadiene from $C_4$ hydrocarbons, reduced capital and equipment costs, reduced use of extractive distillation solvents, and consistency of the purified 1,3-butadiene product.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

The invention claimed is:

1. A system for purifying 1,3-butadiene from a $C_4$ hydrocarbon stream including 1,3-butadiene and one or more acetylenes, comprising:
   an azide-alkyne cycloaddition reactor suitable for an azide-alkyne cycloaddition reaction configured to receive said $C_4$ hydrocarbon stream and an organic azide to generate a first stream comprising 1,3-butadiene and a triazole;
   a first distillation unit coupled to the azide-alkyne cycloaddition reactor configured to separate the triazole from the first stream to produce a second stream comprising 1,3-butadiene; and
   a catalyst suitable for azide-alkyne cycloaddition in said azide-alkyne cycloaddition reactor; wherein the catalyst comprises a member selected from the group consisting of Cu, Au, Ag, Hg, Cd, Zr, Ru, Fe, Co, Ni, Rh, Ti and W.

2. The system of claim 1, wherein the catalyst comprises Cu.

3. The system of claim 1, wherein the catalyst comprises Au.

4. The system of claim 1, wherein the wherein the catalyst comprises Ag.

5. The system of claim 1, wherein the catalyst comprises Hg.

6. The system of claim 1, wherein the catalyst comprises Cd.

7. The system of claim 1, wherein the catalyst comprises Zr.

8. The system of claim 1, wherein the catalyst comprises Ru.

9. The system of claim 1, wherein the catalyst comprises Fe.

10. The system of claim 1, wherein the catalyst comprises Co.

11. The system of claim 1, wherein the catalyst comprises Ni.

12. The system of claim 1, wherein the catalyst comprises Rh.

13. The system of claim 1, wherein the wherein the catalyst comprises W.

14. The system of claim 1, wherein the catalyst comprises Cu and Ni.

* * * * *